US009746400B2

(12) United States Patent
Sagara (10) Patent No.: US 9,746,400 B2
(45) Date of Patent: Aug. 29, 2017

(54) METHOD FOR EVALUATING SEMICONDUCTOR WAFER AND APPARATUS FOR EVALUATING SEMICONDUCTOR WAFER

(71) Applicant: SHIN-ETSU HANDOTAI CO., LTD., Tokyo (JP)

(72) Inventor: Kazuhiro Sagara, Nishigo-mura (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 389 days.

(21) Appl. No.: 14/395,907

(22) PCT Filed: Apr. 15, 2013

(86) PCT No.: PCT/JP2013/002534
§ 371 (c)(1),
(2) Date: Oct. 21, 2014

(87) PCT Pub. No.: WO2013/168360
PCT Pub. Date: Nov. 14, 2013

(65) Prior Publication Data
US 2015/0114132 A1    Apr. 30, 2015

(30) Foreign Application Priority Data
May 7, 2012    (JP) ................................ 2012-105981

(51) Int. Cl.
*G01N 3/02*    (2006.01)
*H01L 21/66*    (2006.01)
(Continued)

(52) U.S. Cl.
CPC ................. *G01N 3/02* (2013.01); *G01N 3/42* (2013.01); *H01L 22/12* (2013.01);
(Continued)

(58) Field of Classification Search
CPC ... G01N 2033/0078; G01N 2033/0095; G01N 2203/006; G01N 2203/0067;
(Continued)

(56) References Cited

U.S. PATENT DOCUMENTS 5,876,819 A      3/1999  Kimura et al.
6,142,010 A *  11/2000  Merck, Jr. ................ G01N 3/42
                                                                     73/81

(Continued)

FOREIGN PATENT DOCUMENTS

JP    A-11-121592        4/1999
JP    A-2000-306966     11/2000
(Continued)

OTHER PUBLICATIONS

Feb. 29, 2016 Office Action issued in Chinese Patent Application No. 201380023869.1.
(Continued)

*Primary Examiner* — Freddie Kirkland, III
(74) *Attorney, Agent, or Firm* — Oliff PLC (57) ABSTRACT

The present invention provides a method for evaluating a semiconductor wafer concerning a breaking strength of a notch portion of the semiconductor wafer, comprising: applying a load to a notch portion of the semiconductor wafer to be evaluated toward the center of the wafer such that the notch portion of the semiconductor wafer is broken; and evaluating the breaking strength of the notch portion. The present invention provides a method and an apparatus for evaluating a semiconductor wafer that can evaluate the breaking strength of a notch portion of a semiconductor wafer with higher precision and higher sensitivity.

24 Claims, 8 Drawing Sheets

(51) Int. Cl.
*G01N 3/42* (2006.01)
*G01N 33/00* (2006.01)

(52) U.S. Cl.
CPC ............... *G01N 2033/0078* (2013.01); *G01N 2033/0095* (2013.01); *G01N 2203/006* (2013.01); *G01N 2203/0067* (2013.01); *G01N 2203/0282* (2013.01); *G01N 2203/04* (2013.01)

(58) Field of Classification Search
CPC ....... G01N 2203/0282; G01N 2203/04; G01N 3/02; G01N 3/42; H01L 22/12
See application file for complete search history.

(56) References Cited

U.S. PATENT DOCUMENTS

| | | | | |
|---|---|---|---|---|
| 6,339,958 | B1* | 1/2002 | Tsui | G01N 3/42 73/150 A |
| 6,691,564 | B2* | 2/2004 | Anderberg | G01N 3/48 73/81 |
| 9,019,498 | B2* | 4/2015 | Sakai | G01N 21/21 356/369 |
| 2006/0186874 | A1* | 8/2006 | Mackin | G01N 3/42 324/754.1 |
| 2007/0187514 | A1 | 8/2007 | Sasaki | |
| 2010/0026997 | A1* | 2/2010 | Hayashi | G01B 11/24 356/237.5 |
| 2015/0097676 | A1* | 4/2015 | Liu | H01L 22/26 340/584 |

FOREIGN PATENT DOCUMENTS

JP    A-2006-287139    10/2006
TW    200732981 A      9/2007

OTHER PUBLICATIONS

Jul. 9, 2013 Search Report issued in International Patent Application No. PCT/JP2013/002534.

Aug. 11, 2015 Search Report issued in Taiwanese Patent Application No. 102115890.

* cited by examiner

METHOD FOR EVALUATING SEMICONDUCTOR WAFER AND APPARATUS FOR EVALUATING SEMICONDUCTOR WAFER

TECHNICAL FIELD

The present invention relates to a method and an apparatus for evaluating a breaking strength of a notch portion of a semiconductor wafer for use in fabrication processes of semiconductor devices and the like.

BACKGROUND ART

Cracks in semiconductor wafers such as silicon wafers, which are materials used in fabrication processes of semiconductor devices, cause a great loss. There is accordingly an increasing need for wafers, for use in device fabrication, that are resistant to cracks.

In fabrication processes of semiconductors and liquid crystals, particularly, processes of dry etching, ion implantation, vapor deposition, and so on, increased processing temperatures, rapidly heating, and rapidly cooling are being promoted, and fabrication processes performed under vacuum and a dry condition are increasing. In addition, since enlargement of the diameter of substrates such as silicon wafers or glass substrates are advanced, impact resistance or the like is further regarded as important.

The cause of breakage of semiconductor wafers, in many cases, is that the edge of the wafers suffers a blow. It is accordingly important to evaluate the impact strength of a notch portion because the strength especially in the vicinity of the notch portion is low.

Since silicon wafers and the like are brittle materials, an evaluation technique for general materials increases variation in measurement. There are no commercially available standard instruments for evaluating and inspecting brittleness of the notch portion of the wafers. Such an apparatus as is disclosed, for example, in Patent Document 1 has been developed.

CITATION LIST

Patent Literature

Patent Document 1: Japanese Unexamined Patent publication (Kokai) No. 2000-306966

SUMMARY OF INVENTION

Technical Problem

According to diligent studies by the present inventor, however, it was revealed that even an evaluation method in Patent Document 1 cannot evaluate the breaking strength of a notch portion of a semiconductor wafer with high precision.

The evaluation method of a wafer in Patent Document 1 will now be briefly described.

Figure 7:
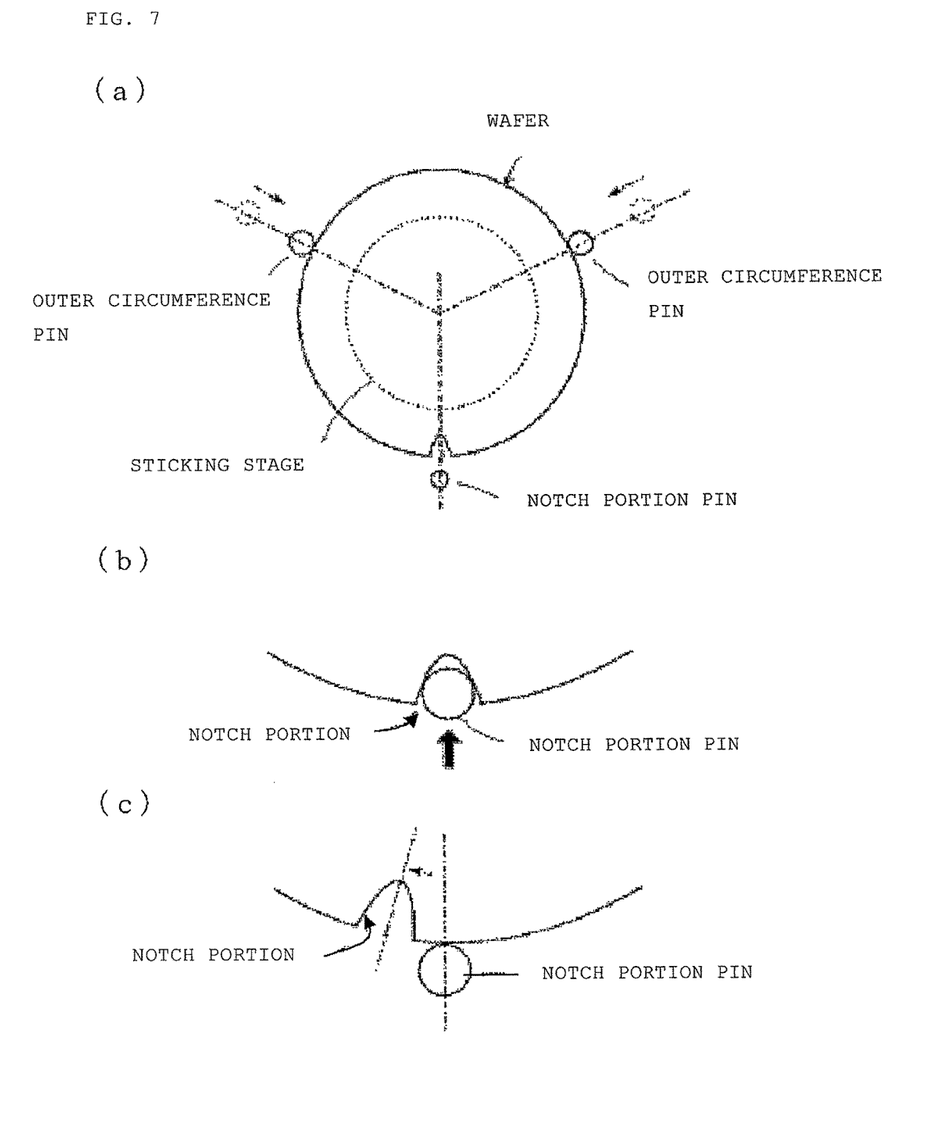
FIG. 7 is an explanatory diagram of an example of a conventional apparatus and method for evaluating the strength of a notch portion of a wafer, wherein (a) is a top view showing the configuration of the evaluation apparatus, (b) is a diagram showing important part in the state where a notch-portion pin is pushed into a V-shaped groove of the notch portion, and (c) is a diagram showing important part in the state where the notch-portion pin is pushed out.

FIG. 7 is an explanatory diagram of an apparatus and a method for evaluating the strength of a notch portion of a wafer, disclosed in Patent Document 1. FIG. 7 at (a) shows a top view of the configuration of the evaluation apparatus. FIG. 7 at (b) shows a diagram of the important part in the state where a notch-portion pin is pushed into a V-shaped groove of the notch portion. FIG. 7 at (c) shows a diagram of the important part in the state where the notch-portion pin is pushed out.

The evaluation apparatus illustrated in FIG. 7 at (a) includes a sticking stage for placing and sticking a wafer to be evaluated thereon, outer circumference pins for placing and centering and pushing the wafer, a notch-portion pin that is to be inserted into the notch-portion of the wafer, and a pressing unit for pressing the outer circumference pins and the notch-portion pin against the wafer.

Moreover, an SiC or super hard pin with an outer diameter of 3 mm (SEMI standard specifications) is used as the notch-portion pin, which is to be inserted into the V-shaped groove that forms the notch-portion provided in the wafer.

In the evaluation, as illustrated in FIG. 7 at (a), the wafer is first placed on the sticking stage, and the position of the wafer is adjusted by the outer circumference pins with the pressing unit to stick and fix the wafer.

Next, as shown in FIG. 7 at (b) and (c), the stage, together with the wafer, is rotated through 1 to 2° with the wafer held by the notch-portion pin and the outer circumference pins for positioning such that the notch-portion pin is pushed out of the V-shaped groove of the notch portion to the outer circumference of the wafer. The stage is then reversely rotated again through 1 to 2° to push the notch-portion pin into the V-shaped groove of the notch portion. This operation is repeated several times. In the configuration in this case, the rotation angles in one direction and the reverse direction may be identical and their values may optionally be set, and the number of repetition of the rotation in one direction and the reverse direction may also be optionally set.

After the completion of the above operation, the wafer is taken out of the stage, and the strength of the edge in the notch portion is evaluated by checking, with a microscope or the like, existence of a fine chip (a particle) in a corner of the notch portion, existence of wear in linear parts of the V-shaped groove of the notch portion and in the corner of the notch portion, the degree of the wear, and so on.

The evaluation method in Patent Document 1 however does not consider effects of anisotropy of crystal such as silicon. The present inventor concerned that the sensitivity and precision are insufficient to evaluate a slight difference in the strength of the notch portion.

Since silicon wafers are brittle materials, an evaluation technique for general materials increases variation in measurement. In addition, there is no JIS standard about evaluation of the strength anisotropy of silicon wafers as above.

Notches are formed in wafers to indicate a crystal orientation. The location of the notches differs in many cases depending on users.

Figure 8:
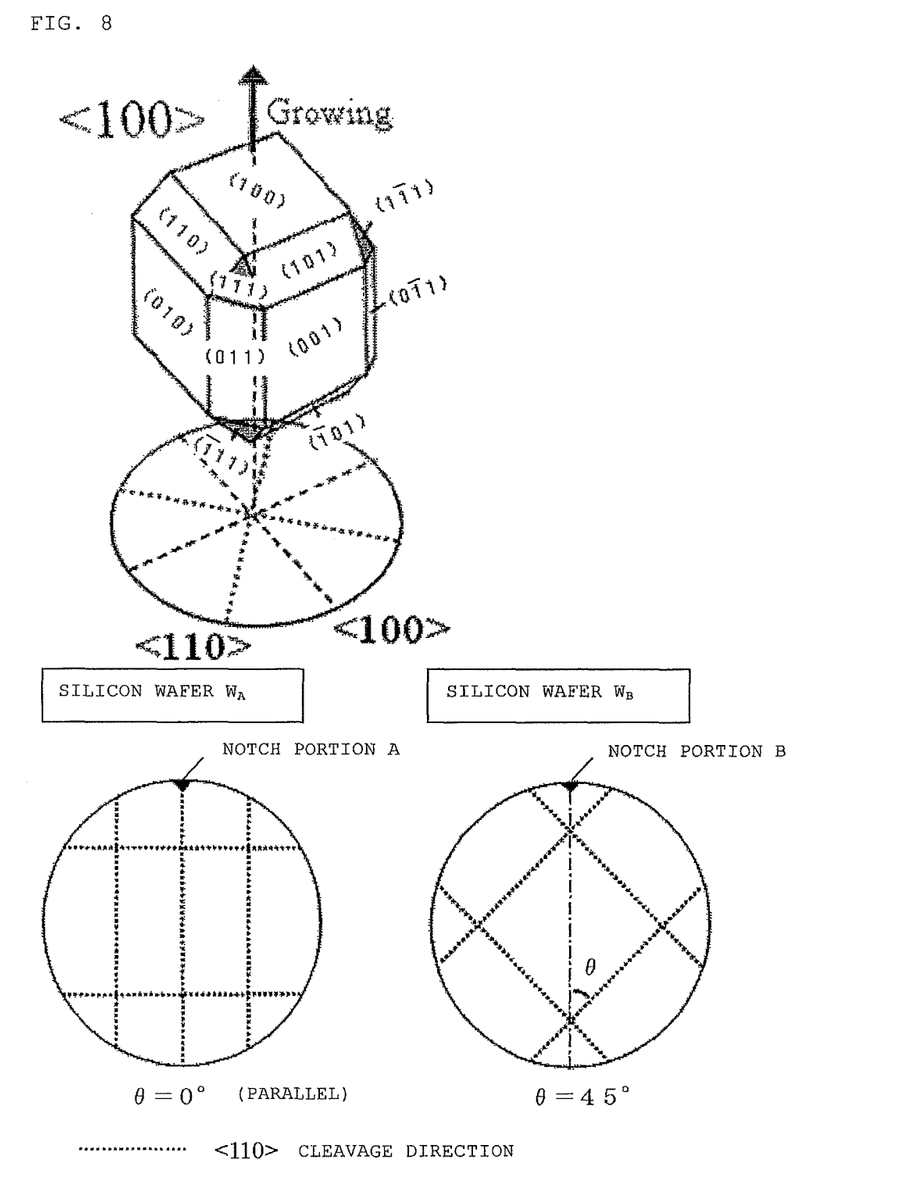
FIG. 8 is a diagram showing representative locations of notch portions of (100) silicon wafers.

FIG. 8 shows representative locations of notch portions of (100) silicon wafers.

As shown in FIG. 8, it is commonly located such that either "the angle θ between the orientation of the notch portion A and the <110> cleavage direction is 0° (silicon wafer $W_A$)" or "the angle θ between the orientation of the notch portion B and the <110> cleavage direction is 45° (silicon wafer $W_B$)".

Silicon, on the other hand, is crystal of a cubic system with a diamond structure, and has anisotropy of physical properties such as Young's modulus. Young's modulus at a portion having an angle θ of 0° to the <110> cleavage direction is about 169 GPa. Young's modulus at a portion having an angle θ of 45° to the <110> cleavage direction is about 130 GPa.

Accordingly, the breaking strength of the notch portion A greatly differs from that of the notch portion B. The effect of anisotropy is clearly seen in the form of breaking.

There are however no documents describing the effect of anisotropy on breaking strength.

The present invention was accomplished in view of the above-described problems. It is an object of the present invention to provide a method and an apparatus for evaluating a semiconductor wafer that can evaluate the breaking strength of a notch portion of a semiconductor wafer with higher precision and higher sensitivity.

Solution to Problem

To achieve the above object, the present invention provides a method for evaluating a semiconductor wafer concerning a breaking strength of a notch portion of the semiconductor wafer, comprising: applying a load to the notch portion of the semiconductor wafer to be evaluated toward the center of the wafer such that the notch portion of the semiconductor wafer is broken; and evaluating the breaking strength of the notch portion.

The inventive method for evaluating a semiconductor wafer can detect a difference due to the anisotropy of crystal orientation, which cannot be detected by the conventional evaluation method, thereby enabling highly precise and highly sensitive evaluation of the breaking strength of the notch portion. The method can thereby evaluate, for example, where the notch portion ought to be formed in the wafer to increase the strength of the notch portion.

In the method, the load can be applied by pressing a pin against the notch portion.

In this manner, the breaking strength can readily be evaluated by applying the load with the pin.

Moreover, the load can be applied in a manner of a vertical static pressure load or a horizontal static pressure load.

In this manner, the breaking strength can efficiently be evaluated with better precision.

Moreover, the breaking strength of the notch portion can be evaluated in such a manner that a test piece including the notch portion is cut from the semiconductor wafer to be evaluated; the test piece is interposed and held between a pair of holding jigs; and a load is applied to the notch portion of the held test piece.

Such a method can inhibit effects on measurement results, for example, due to flexion of the test piece when the load is applied, thereby accurately evaluating the breaking strength.

Moreover, each of the pair of holding jigs may be provided with a cut through which a vicinity of the notch portion is exposed.

With such holding jigs, a portion other than the portion to which the load is applied can be interposed and held between the holding jigs, and effects on measurement results, for example, due to flexion of the test piece can be more reliably prevented.

Moreover, in addition to the evaluation of the breaking strength of the notch portion of the semiconductor wafer by using the test piece including the notch portion, the method can include cutting a test piece including no notch portion from the semiconductor wafer to be evaluated; applying a load to an edge of the test piece including no notch portion; evaluating a breaking strength of the edge of the semiconductor wafer; and comparing evaluation results of the notch portion and the edge.

Such a method can also evaluate, for example, the breaking strength of the edge of the same semiconductor wafer, compare the breaking strength between the notch portion and the edge, and obtain various data concerning the breaking strength of the notch portion, so more detailed evaluation can be made.

Furthermore, the present invention provides an apparatus for evaluating a semiconductor wafer, the apparatus being configured to evaluate a breaking strength of a notch portion of the semiconductor wafer comprising a load applying device configured to apply a load to the semiconductor wafer to be evaluated, the load applying device applying the load in a direction from the notch portion to the center of the wafer and being capable of breaking the notch portion by the load.

The inventive apparatus for evaluating a semiconductor wafer can detect a difference due to the anisotropy of crystal orientation, which cannot be detected by the conventional evaluation apparatus, thereby enabling highly precise and highly sensitive evaluation of the breaking strength of the notch portion. The apparatus can thereby evaluate, for example, where the notch portion ought to be formed in the wafer to increase the strength of the notch portion.

In the apparatus, the load applying device can include a pin configured to apply the load by being pressed against the notch portion.

Such an apparatus can readily evaluate the breaking strength by applying the load with the pin.

Moreover, the load applying device can be configured to apply the load in a manner of a vertical static pressure load or a horizontal static pressure load.

In this manner, the breaking strength can efficiently be evaluated with better precision.

Moreover, the apparatus can further include a pair of holding jigs configured to interpose and hold a test piece therebetween, the test piece including the notch portion and being cut from the semiconductor wafer to be evaluated.

Such an apparatus can inhibit effects on measurement results, for example, due to flexion of the test piece when the load is applied, thereby accurately evaluating the breaking strength.

Moreover, each of the pair of holding jigs may be provided with a cut through which a vicinity of the notch portion is exposed.

With such holding jigs, the apparatus can interpose and hold a portion other than the portion to which the load is applied between the holding jigs, and more reliably prevent effects on measurement results, for example, due to flexion of the test piece.

Moreover, the load applying device can be configured to be further capable of applying a load to an edge of a test piece and breaking the edge by the load, the test piece including no notch portion and being cut from the semiconductor wafer to be evaluated.

Such an apparatus can also evaluate, for example, the breaking strength of the edge of the same semiconductor wafer, compare the breaking strength between the notch portion and the edge, and obtain various data concerning the breaking strength of the notch portion, so more detailed evaluation can be made.

Advantageous Effects of Invention

As described above, the inventive method and apparatus for evaluating a semiconductor wafer can evaluate the breaking strength of a notch portion of a semiconductor wafer with higher precision and higher sensitivity.

DESCRIPTION OF EMBODIMENTS

An embodiment of the inventive method and apparatus for evaluating a semiconductor wafer will now be described in detail with reference to figures, but the present invention is not limited to this embodiment.

Figure 1:
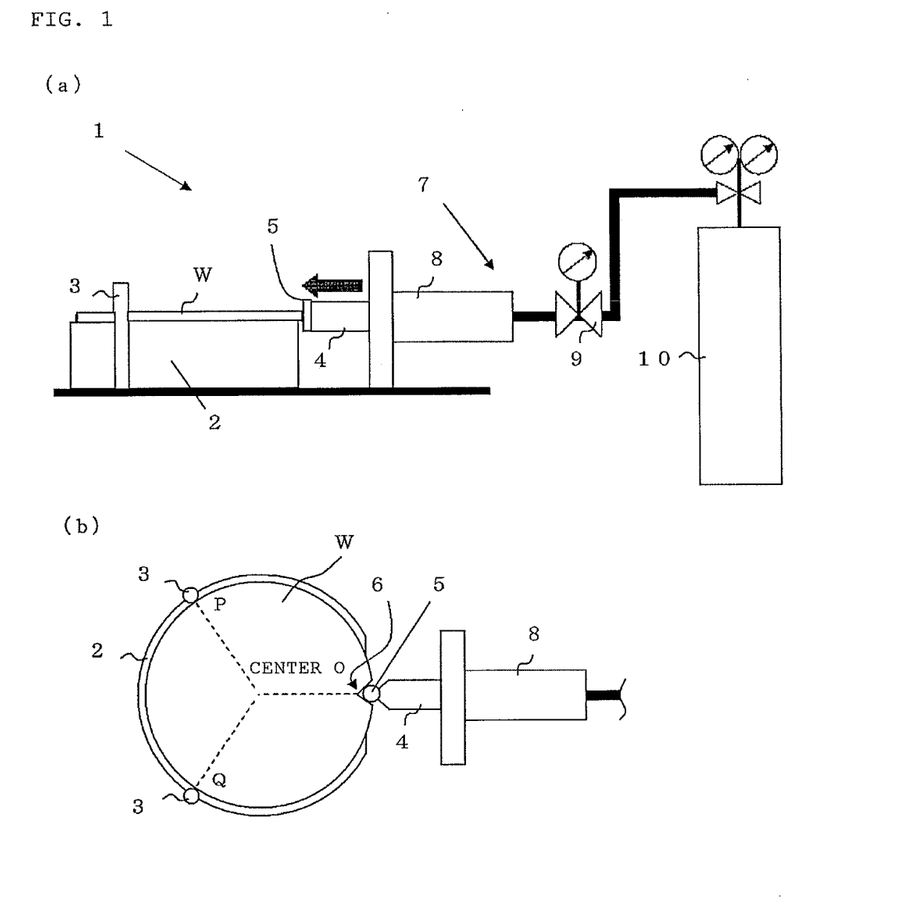
FIG. 1 is a schematic diagram of an example of the inventive apparatus for evaluating a semiconductor wafer, wherein (a) is a side view, and (b) is a plan view of part of the apparatus.

FIG. 1 schematically illustrates an example of the inventive apparatus for evaluating a semiconductor wafer, wherein (a) shows a side view, and (b) shows a plan view of part of the apparatus.

The evaluation apparatus 1 includes a mount 2 for placing a semiconductor wafer (also referred to simply as a wafer, hereinafter) W thereon, supports 3 that are provided in the mount 2 and support the wafer W at locations including at least two points P, Q on the wafer circumference; and a load applying device 7 for applying a static pressure load toward the center O of the wafer W in a manner that a load shaft 4 is moved in a horizontal direction, and a pin 5 attached to the end thereof is pressed against a notch portion 6 of the wafer W.

Here, the mount 2 is not particularly limited, provided it can place the wafer W thereon. In addition, as illustrated in FIG. 1, the mount 2 preferably places the wafer W horizontally thereon and the load applying device 7 preferably moves the load shaft 4 horizontally, because this configuration enables the apparatus to readily place the wafer W and to accurately apply a static pressure load toward the wafer center.

The present invention however is not limited thereto. Provided the apparatus can apply a static pressure load toward the wafer center, the mount 2 may place the wafer W, for example, in a slanted manner or vertically, and the load applying device 7 may impart parallel motion to the load shaft 4 in a slanting direction or vertically (in a manner of a vertical static pressure load).

The supports 3 are also not particularly limited, provided the supports can support the wafer W when a static pressure load is applied to the wafer W. The shape may be, for example, cylindrical. The material may be, for example, metal such as stainless steel, such metal coated with resin and so on, or ceramics such as SiC.

The load applying device 7 including the load shaft 4 and pin 5 is also not particularly limited, provided the device can apply a static pressure load to the wafer W with the load shaft 4 and break the notch portion 6 of the wafer W by control of the load. The load applying device 7 preferably includes, for example, an air cylinder 8 and a pressure controlling valve 9 and moves the load shaft 4 with the air cylinder 8 to control the static pressure load with the pressure controlling valve 9, because this configuration enables the apparatus to smoothly apply a more accurate static pressure load to the wafer W with a simple structure. The pressure controlling valve 9, for example, is connected to an Ar gas cylinder 10.

Here, the load shaft 4 may be configured to be capable of pressing the pin 5 attached to its end against the notch portion 6 of the wafer W to apply the static pressure load. The shape of the load shaft 4 may be, for example, prismatic and its end may have wedge shape. It need only be capable of properly attaching and fixing the pin 5. If the pin 5 is not attached, then it need only have an end that can press the notch portion 6 of the wafer W. As in the supports, the material may be, for example, metal such as stainless steel, such metal coated with resin and so on, or ceramics such as SiC.

Figure 2:
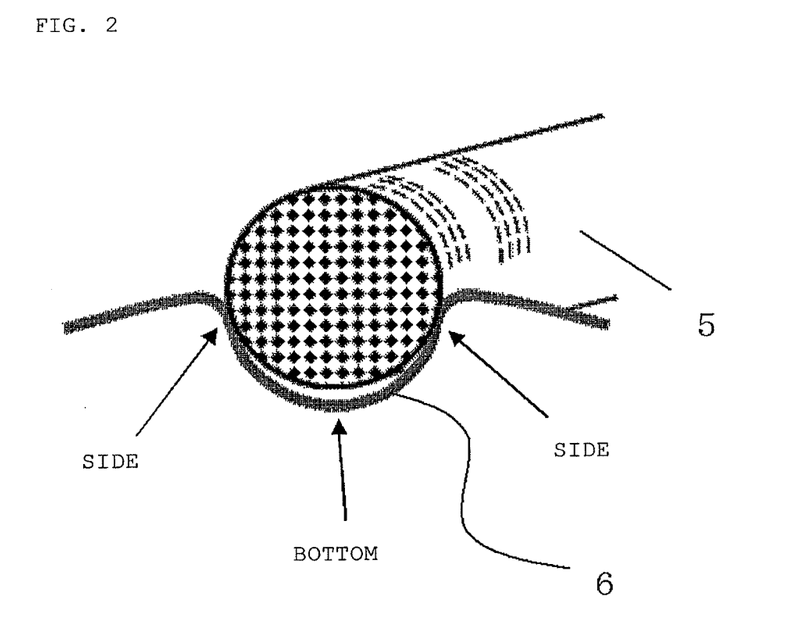
FIG. 2 is a schematic diagram of an exemplary pin.

FIG. 2 shows an example of the pin 5.

The pin 5 need only enable application of a static pressure load by being inserted into the notch portion 6 of the wafer W. The material is preferably, but not particularly limited to, SiC, which is harder than silicon.

In addition, the shape thereof may for example be, but not particularly limited to, cylindrical. Its diameter is not particularly limited, but preferably adjusted such that when the pin 5 is pushed into the notch portion 6, the pin 5 contacts two sides of the notch portion 6 but does not contact the bottom of the notch portion 6. Such adjustment of its size enables the pin to prevent from becoming very thin and hence susceptive to damage due to lack of the pin strength. In addition, since the bottom of the notch portion 6 has many points of inflection, lack of the degree of surface polish is apt to lead to lack of its strength. For this reason, it is difficult to perform accurate positioning and measurement results vary. This is a reason for the above adjustment.

As illustrated in FIG. 1, the above supports 3 and the load applying device 7 are preferably configured to be disposed such that at least the two points P, Q on the outer circumference of the wafer W supported by the supports 3 and the notch portion 6 of the wafer against which the pin 5 is pressed are located at equal angular intervals with respect to the wafer center O, because this configuration enables the apparatus to apply the static pressure load more uniformly to a semiconductor wafer and to more accurately measure the mechanical strength. More specifically, in FIG. 1, since the supported points are two points P, Q, in this case, the points P, Q, and the notch portion 6 are each disposed at an equal angular interval of 120° with respect to the wafer center O. In this case, the supports 3 are preferably capable of adjusting its position according to the diameter of a wafer so that, as described above, the supported points and the like can be disposed at equal angular intervals also with respect to the center of another wafer having a different diameter.

In the above description, the evaluation apparatus 1 applies a load to the notch portion 6 while holing the whole wafer W. The present invention however is not limited thereto. In another embodiment, the evaluation apparatus can also apply a load while holding a test piece cut from the wafer W so as to have a portion including the notch portion 6.

Figure 3:
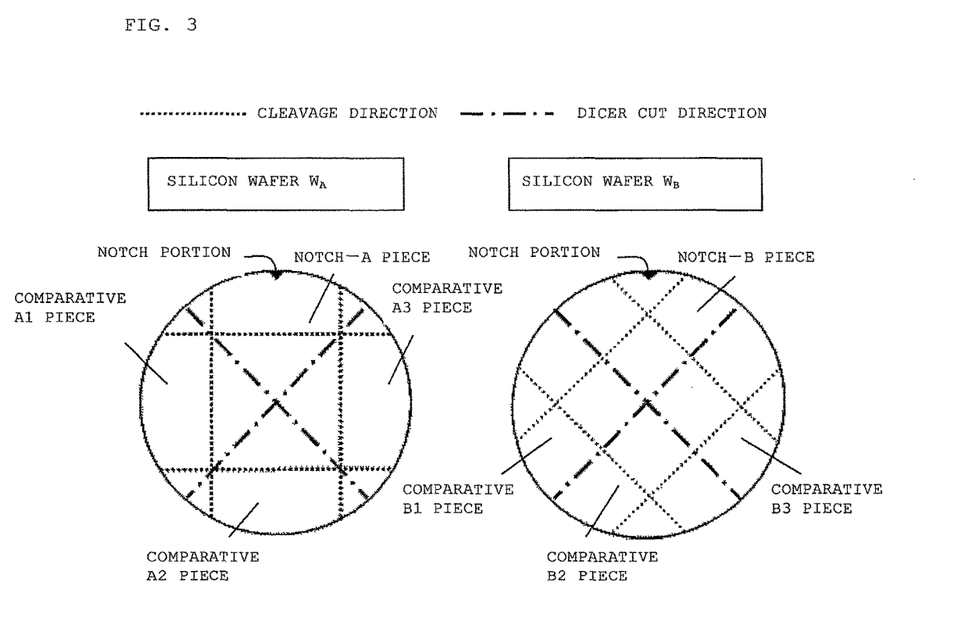
FIG. 3 is an explanatory diagram of an exemplary test piece.

FIG. 3 shows examples of the test piece to be evaluated in this case. Two test pieces cut from the two (100) silicon wafers $W_A$, $W_B$ shown in FIG. 8, as described above, are shown. Each of the whole wafers is divided crosswise into 4 test pieces with a dicer such that a notch portion locates at the center of an arc of one of the test pieces. The four test pieces are thus obtained from each wafer. One of the test pieces includes the notch portion (a notch-A piece and a notch-B piece). As described later, the other three pieces including no notch portion can be used, for example, in comparative example (comparative A1-A3 pieces and comparative B1-B3 pieces).

Regarding the test pieces, their shape and the number of test pieces cut from a wafer are not limited. Proper test pieces may be prepared depending on how to evaluate and so on.

Figure 4:
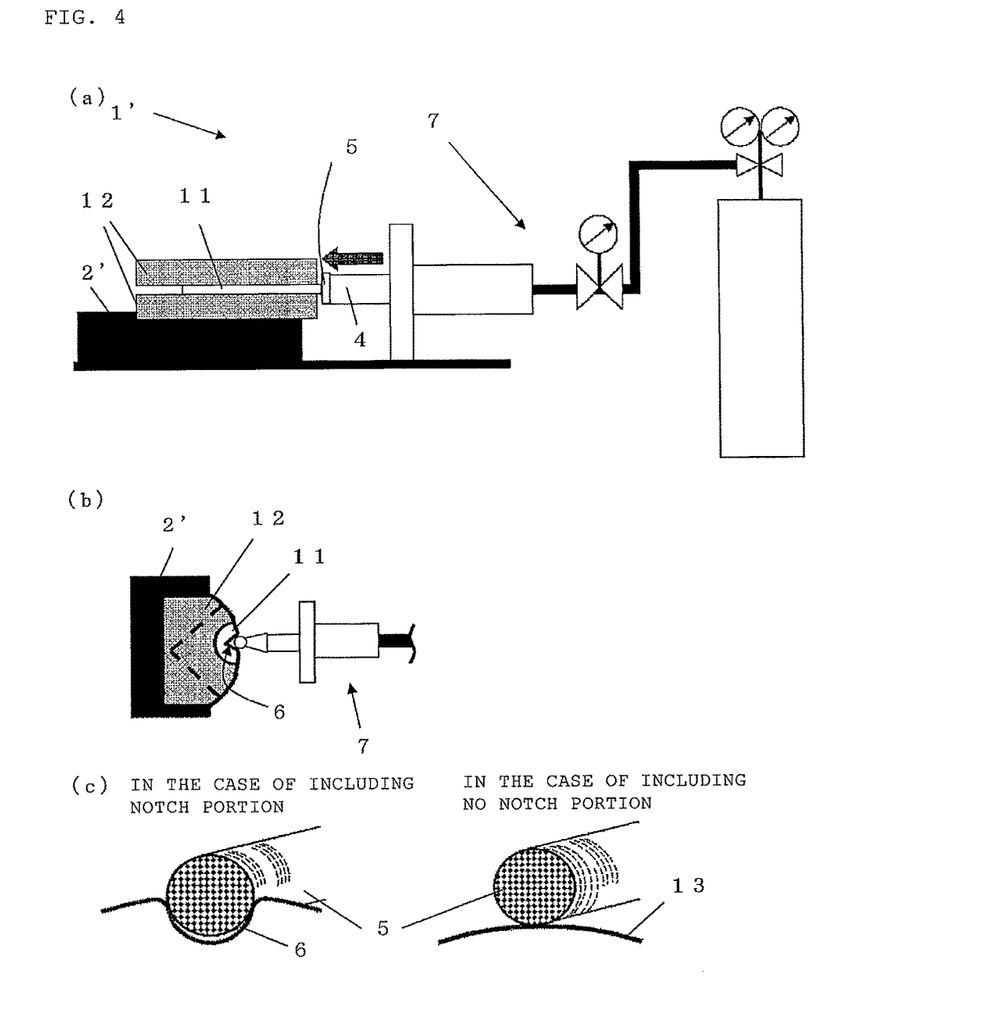
FIG. 4 is a schematic diagram of another example of the inventive apparatus for evaluating a semiconductor wafer, wherein (a) is a side view, (b) is a plan view of part of the apparatus, and (c) is an explanatory diagram showing the position of a pin pressed against a notch portion or an edge.

FIG. 4 illustrates another apparatus for evaluating such a test piece, which is referred to as the evaluation apparatus 1', wherein (a) is a side view, (b) is a plan view of part of the apparatus, and (c) shows the position of a pin pressed against a notch potion or an edge.

The evaluation apparatus 1' includes a pair of holding jigs 12 for holding a test piece 11 of the wafer W, a mount 2' for placing and fixing the holding jigs 12, and a load applying device 7. The load applying device 7 may be, for example, the same as in the evaluation apparatus 1 in FIG. 1. It need only be capable of apply a load to the test piece 11 to break the test piece by the load.

This apparatus can apply a load not only to the test piece including the notch portion 6 (the notch-A piece or the notch-B piece), but also to the edge of the test piece including no notch portion 6 (the comparative A1-A3 pieces and the comparative B1-B3 pieces). Such an apparatus enables evaluation of both the breaking strengths of the notch portion 6 of a wafer and the edge of the same wafer, and comparison between the breaking strengths of the notch portion 6 and the edge 13, thereby enabling more detailed evaluation of the breaking strength of the notch portion 6.

Figure 5:
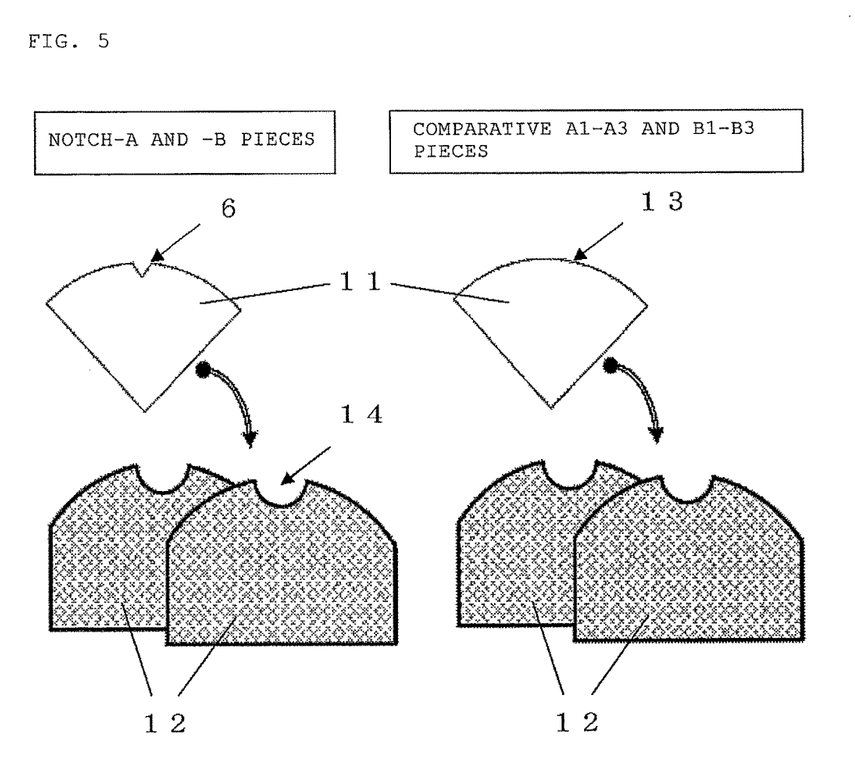
FIG. 5 is a schematic diagram of an exemplary pair of holding jigs.

FIG. 5 shows an example of a pair of holding jigs 12.

The pair of holding jigs 12 interposes and holds the test piece 11 therebetween with a given force and is fixed on the mount 2'. The pair of holding jigs 12 need only be capable of reliably holding the test piece 11 when a load is applied to the test piece 11, and its shape and material are not particularly limited.

In specific examples of the pair of holding jigs, a base of a toggle clamp can be attached to one of the holding jigs 12 and the test piece and the other holding jig 12 are clamped and held by the toggle clamp.

In addition, the pair of holding jigs 12 may be provided with a cut 14 through which the vicinity of the notch portion 6 of the test piece (the notch-A piece or the notch-B piece) is exposed. Such a pair of holding jigs 12 enables reliable prevention of buckling due to flexion because the holding jigs 12 can expose the vicinity of the notch portion 6 to which a load is applied and thereby interpose and hold the other portion therebetween without being interfered with the load applying device 7.

Incidentally, even in the case of the comparative A1-A3 piece and comparative B1-B3 piece, forming such a cut 14 eliminates the possibility of interference between the pin 5 pushing the edge 13 etc., and the pair of holding jigs 12.

The mount 2' need only be capable of fixing the pair of holding jigs 12 that interposes and holds the wafer W, and is not particularly limited. It can be configured, for example, such that the pair of holding jigs 12 is engaged with a recess formed thereon and thereby fixed.

The apparatus 1, 1' can evaluate the breaking strength of the notch portion 6 in more detail with higher sensitivity and higher precision than a conventional apparatus. In particular, even a slight difference in the breaking strength due to a difference in the orientation of the notch portion can also be evaluated.

Next, procedures for implementing the inventive evaluation method with the inventive evaluation apparatus 1 illustrated in FIG. 1 will be described.

The semiconductor wafer to be evaluated may be, for example, a silicon wafer or a compound semiconductor wafer and its kind and diameter are not particularly limited. In addition to silicon, sapphire and SiC crystal, which are used as semiconductor wafers, also have the anisotropy of physical properties such as Young's modulus. Naturally, the strength of a notch portion of a wafer made of a material other than these materials can be evaluated.

Prepared wafer W is placed on the mount 2. While the wafer W is supported at locations including at least two points P, Q on the wafer circumference by the supports 3 provided in the mount 2, parallel motion is imparted to the load shaft 4 of the load applying device 7 to press the pin 5 attached to the end of the load shaft 4 against the notch portion 6 of the wafer W, and a static pressure load is applied toward the center O of the wafer W. The applied static pressure load is increased and a value of the static pressure load when the notch portion 6 of the wafer W is broken is measured to evaluate the breaking strength.

In this manner, since the breaking strength, which is a mechanical strength, can be quantitatively measured, the evaluation and the analysis of the measured breaking strength can contribute to development of semiconductor wafers in which their crack is hard to occur during handling in device processes. In particular, it is possible to evaluate where the notch portion ought to be formed (i.e., where the notch portion ought to be oriented) to increase the strength of the notch portion.

In addition, procedures for implementing the inventive evaluation method with the other exemplary evaluation apparatus 1' of the invention illustrated in FIG. 4 will be described.

A test piece 11, as a subject to be evaluated, is cut from a semiconductor wafer. The cutting method is not particularly limited. The test piece 11 can be obtained by dividing the wafer into four pieces (a set of a notch-A piece and comparative A1-A3 pieces, or a set of a notch-B piece and comparative B1-B3 pieces), for example, as shown in FIG. 3.

Figure 6:
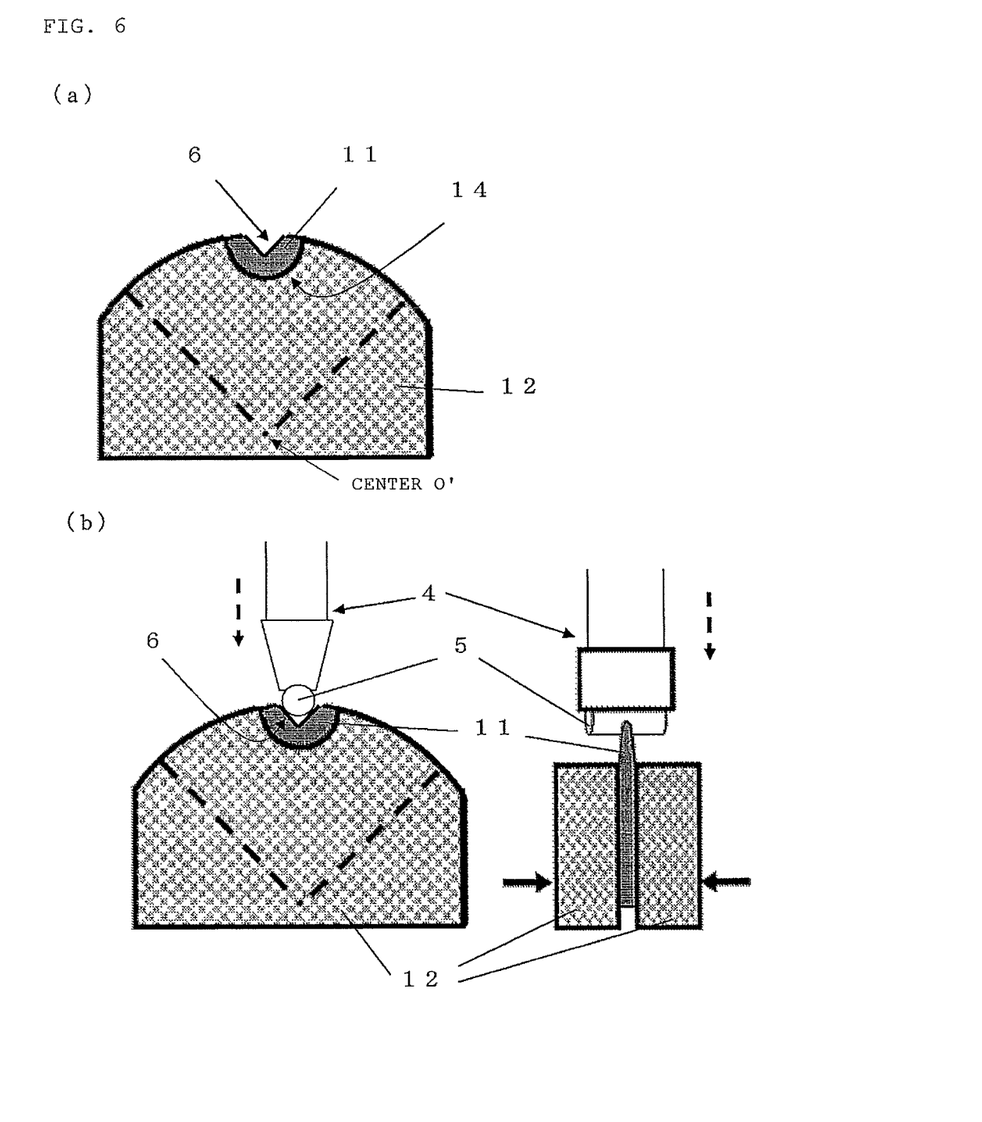
FIG. 6 is an explanatory diagram of an exemplary evaluation method with holding jigs, wherein (a) is an explanatory diagram showing how to hold a test piece, and (b) is an explanatory diagram showing how to apply a load.

FIG. 6 shows an exemplary evaluation method with the holding jigs 12, wherein (a) shows how to hold the test piece 11, and (b) shows how to apply a load.

In the evaluation of a test piece including the notch portion 6 (the notch-A piece and the notch-B piece), as shown in FIG. 6 at (a) and (b), the test piece is first interposed and held between the pair of holding jigs 12 such that the vicinity of the notch portion 6 is exposed through the cut 14. In this manner, a portion other than the portion to which the load is applied can be interposed and held between the holding jigs 12, and the effect on measurement results, for example, due to flexion of the test piece 11 can reliably be prevented.

As shown in FIG. 4 at (a), the holding jigs 12 and all are placed on the mount 2' and as shown in FIG. 6 at (b), parallel motion is then imparted to the load shaft 4 of the load applying device 7 to press the pin 5 attached to the end of the load shaft 4 against the notch portion 6 of the test piece, and a static pressure load is applied. The applied static pressure load is increased and a value of the static pressure load when the notch portion 6 of the test piece is broken is measured to evaluate the breaking strength.

At this time, the holding way with the holding jigs 12, the placing way on the mount 2', the movement direction of the load shaft 4, and so on are adjusted to properly direct the load toward O' of the test piece 11 (corresponding to the center O of a wafer).

It is also possible to evaluate the breaking strength of, for example, a portion other than the notch portion 6 to be compared with the measurement result of the notch portion 6.

When a test piece including no notch portion 6 (the comparative A1-A3 pieces and the comparative B1-B3 pieces) is evaluated, the test piece is held with the pair of holding jigs 12 and placed on the mount 2', parallel motion is imparted to the load shaft 4 of the load applying device 7, the pin 5 attached to the end of the load shaft 4 is pressed against the edge 13 of the test piece, and a static pressure load is applied toward a point corresponding to the center O of a wafer. The applied static pressure load is increased and a value of the static pressure load when the edge 13 of the test piece is broken is measured to evaluate the breaking strength.

In this manner, the evaluation result of the edge 13 can also be obtained. Comparing this evaluation result with the evaluation result of the notch portion 6 enables various detailed evaluations of the breaking strength of the notch portion 6.

EXAMPLE

The present invention will now be more specifically described with reference to Example and Comparative Example, but the present invention is not limited to this example.

Example

Two kind of silicon wafers were prepared as sample wafers to be evaluated. Both types were silicon wafers having a diameter of 300 mm, a thickness of 0.78 mm, a (100) orientation, a P-type, an oxygen concentration of 12 ppma, and a resistivity of 20 Ωcm, but different notch portion orientations. More specifically, as shown in FIG. 8, one type was a silicon wafer $W_A$ in which the angle θ between the orientation of the notch portion A and the <110> cleavage direction was 0°, the other type was a silicon wafer $W_B$ in which the angle θ between the orientation of the notch portion B and the <110> cleavage direction was 45°, and 25 wafers were prepared in each type.

As shown in FIG. 3, each of these wafers was cut crosswise into 4 pieces with a dicer such that a notch portion located at the center of an arc of one of the test pieces, so four test pieces (silicon pieces) having a fan shape were produced per wafer. In this way, samples of notch-A piece, comparative A1-A3 pieces, notch-B piece, and comparative B1-B3 pieces, which were differentiated by the existence of notch and the orientation of the crystal axis were prepared.

With the evaluation apparatus 1' illustrated in FIG. 4, the silicon piece thus produced was firmly interposed and held between a pair of the holding jigs 12. The load shaft 4 was then horizontally moved to press the pin 5 attached to the end thereof against the notch portion of the silicon piece or the edge at a given position. A cylindrical pin that was made of SiC and had an outer diameter of 3 mm and a length of 20 mm was used as the pin 5.

The parallel motion was further imparted to the load shaft 4 to apply a static pressure load to the silicon piece so that the breaking load (N) when the silicon piece was broken was measured.

The breaking load in each case is summarized in Table 1.

TABLE 1

| BREAKING LOAD | NOTCH-A PIECE | COMPARATIVE A1-A3 PIECES | NOTCH-B PIECE | COMPARATIVE B1-B3 PIECES |
|---|---|---|---|---|
| MEAN VALUE | 733 | 716 | 820 | 962 |
| STANDARD DEVIATION | 65 | 137 | 83 | 102 |

As shown Table 1, a significant difference was clearly seen in a population mean when the population mean was tested (a significant level was 0.05) from the distribution of the breaking strength of the "notch-A piece" and the "notch-B piece". It is understood that this was caused by the anisotropy of the crystal orientation of the wafers. The mean value for the "notch-A piece" was 733N, whereas the mean value for the "notch-B piece" was a higher value of 820N. It is understood that the "notch-B piece" was harder to break. It is accordingly understood that forming a notch portion as in the silicon wafer $W_B$ increases the strength.

For the "comparative A1-A3 pieces" and the "comparative B1-B3 pieces", a significant difference was clearly seen in a population mean when the population mean was tested (a significant level was 0.05) between the "comparative A1-A3 pieces" and "comparative B1-B3 pieces", regardless of the same circumferential shape and polished surface condition. The mean value for the "comparative A1-A3 pieces" was 716N, whereas the mean value for the "comparative B1-B3 pieces" was a higher value of 962N. It is understood that the "comparative B1-B3 pieces" were harder to break.

Comparison between the "notch-A piece" (733N) and the "comparative A1-A3 pieces" (716N) revealed that the "notch-A piece" had a higher mean value of the breaking load and was harder to break. In contrast, Comparison between the "notch-B piece" (820N) and the "comparative B1-B3 pieces" (962N) revealed that the "comparative B1-B3 pieces" had a higher mean value of the breaking load and were harder to break.

In other words, it is understood that in the wafer $W_A$, the notch portion had a higher strength than the edge, but in the wafer $W_B$, the edge had a higher strength than the notch portion. The inventive evaluation apparatus and method were able to check a variation in the strength due to a difference in the orientation of the notch portion.

Comparative Example

The same sample wafers (25 of the silicon wafers $W_A$ and 25 of the silicon wafers $W_B$) as in Example were prepared.

The breaking strength of the notch portion of these sample wafers was evaluated with a conventional evaluation apparatus illustrated in FIG. 7.

The wafer was placed on a sticking stage of the evaluation apparatus in FIG. 7. The position of the wafer was adjusted by the outer circumference pins to stick and fix the wafer on the stage. A 3-mm-outer-diameter SiC pin was used as a notch-portion pin. The notch-portion pin was pressed against the notch portion with a force of 1.5 kgf (14.7N).

While the notch portion pin was pressed against the notch portion, the wafer was rotated through a prescribed angle of 2° in one direction and the reverse direction by turns such that, as shown in FIG. 7 at (b) and (c), the notch-portion pin was pushed out of the V-shaped groove of the notch portion to the outer circumference and then the notch-portion pin was pushed into the notch portion. This operation was repeated five times.

The corner of the notch portion was then observed with a microscope to check the number of wafers in which a fine chip occurred.

The conventional evaluation method revealed that the number of wafers in which a fine chip occurred was four in the silicon wafer $W_A$ and four in the silicon wafer $W_B$. That is, no difference in the strength between the notch portion A and the notch portion B was seen.

As described above, the conventional evaluation apparatus and method was not able to check a variation in the strength due to a difference in the orientation of the notch portion.

Accordingly, the present invention enables detailed evaluation of a notch portion, such as, for example, strength variation due to the anisotropy of the orientation of the notch portion, which cannot be evaluated by the conventional method, thereby enabling evaluation with higher sensitivity and higher precision.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A method for evaluating a semiconductor wafer concerning a breaking strength of a notch portion of the semiconductor wafer, comprising:
    applying a load to the notch portion of the semiconductor wafer to be evaluated toward the center of the wafer such that the notch portion of the semiconductor wafer is broken; and
    evaluating the breaking strength of the notch portion.

2. The method for evaluating a semiconductor wafer according to claim 1, wherein the load is applied by pressing a pin against the notch portion.

3. The method for evaluating a semiconductor wafer according to claim 2, wherein the load is applied in a manner of a vertical static pressure load or a horizontal static pressure load.

4. The method for evaluating a semiconductor wafer according to claim 3, wherein the breaking strength of the notch portion is evaluated in such a manner that a test piece including the notch portion is cut from the semiconductor wafer to be evaluated; the test piece is interposed and held between a pair of holding jigs; and a load is applied to the notch portion of the held test piece.

5. The method for evaluating a semiconductor wafer according to claim 4, wherein each of the pair of holding jigs is provided with a cut through which a vicinity of the notch portion is exposed.

6. The method for evaluating a semiconductor wafer according to claim 5, further comprising: in addition to the evaluation of the breaking strength of the notch portion of the semiconductor wafer by using the test piece including the notch portion, cutting a test piece including no notch portion from the semiconductor wafer to be evaluated; applying a load to an edge of the test piece including no notch portion; evaluating a breaking strength of the edge of the semiconductor wafer; and comparing evaluation results of the notch portion and the edge.

7. The method for evaluating a semiconductor wafer according to claim 2, wherein the breaking strength of the notch portion is evaluated in such a manner that a test piece including the notch portion is cut from the semiconductor wafer to be evaluated; the test piece is interposed and held between a pair of holding jigs; and a load is applied to the notch portion of the held test piece.

8. The method for evaluating a semiconductor wafer according to claim 1, wherein the load is applied in a manner of a vertical static pressure load or a horizontal static pressure load.

9. The method for evaluating a semiconductor wafer according to claim 8, wherein the breaking strength of the notch portion is evaluated in such a manner that a test piece including the notch portion is cut from the semiconductor wafer to be evaluated; the test piece is interposed and held between a pair of holding jigs; and a load is applied to the notch portion of the held test piece.

10. The method for evaluating a semiconductor wafer according to claim 1, wherein the breaking strength of the notch portion is evaluated in such a manner that a test piece including the notch portion is cut from the semiconductor wafer to be evaluated; the test piece is interposed and held between a pair of holding jigs; and a load is applied to the notch portion of the held test piece.

11. The method for evaluating a semiconductor wafer according to claim 10, wherein each of the pair of holding jigs is provided with a cut through which a vicinity of the notch portion is exposed.

12. The method for evaluating a semiconductor wafer according to claim 10, further comprising: in addition to the evaluation of the breaking strength of the notch portion of the semiconductor wafer by using the test piece including the notch portion, cutting a test piece including no notch portion from the semiconductor wafer to be evaluated; applying a load to an edge of the test piece including no notch portion; evaluating a breaking strength of the edge of the semiconductor wafer; and comparing evaluation results of the notch portion and the edge.

13. An apparatus for evaluating a semiconductor wafer, the apparatus being configured to evaluate a breaking strength of a notch portion of the semiconductor wafer comprising
    a load applying device configured to apply a load to the semiconductor wafer to be evaluated, the load applying device applying the load in a direction from the notch portion to the center of the wafer and being capable of breaking the notch portion by the load.

14. The apparatus for evaluating a semiconductor wafer according to claim 13, wherein the load applying device includes a pin configured to apply the load by being pressed against the notch portion.

15. The apparatus for evaluating a semiconductor wafer according to claim 14, wherein the load applying device is configured to apply the load in a manner of a vertical static pressure load or a horizontal static pressure load.

16. The apparatus for evaluating a semiconductor wafer according to claim 15,
further comprising a pair of holding jigs configured to interpose and hold a test piece of the semiconductor wafer to be evaluated therebetween, the test piece including the notch portion,
wherein the load applying device is configured to apply the load to the test piece held by the pair of holding jigs.

17. The apparatus for evaluating a semiconductor wafer according to claim 16, wherein each of the pair of holding jigs is provided with a cut through which a vicinity of the notch portion is exposed.

18. The apparatus for evaluating a semiconductor wafer according to claim 17, wherein the load applying device is further capable of applying a load to an edge of a test piece and breaking the edge by the load, the test piece including no notch portion and being cut from the semiconductor wafer to be evaluated.

19. The apparatus for evaluating a semiconductor wafer according to claim 14,
further comprising a pair of holding jigs configured to interpose and hold a test piece of the semiconductor wafer to be evaluated therebetween, the test piece including the notch portion,
wherein the load applying device is configured to apply the load to the test piece held by the pair of holding jigs.

20. The apparatus for evaluating a semiconductor wafer according to claim 13, wherein the load applying device is configured to apply the load in a manner of a vertical static pressure load or a horizontal static pressure load.

21. The apparatus for evaluating a semiconductor wafer according to claim 20,
further comprising a pair of holding jigs configured to interpose and hold a test piece of the semiconductor wafer to be evaluated therebetween, the test piece including the notch portion,
wherein the load applying device is configured to apply the load to the test piece held by the pair of holding jigs.

22. The apparatus for evaluating a semiconductor wafer according to claim 13,
further comprising a pair of holding jigs configured to interpose and hold a test piece of the semiconductor wafer to be evaluated therebetween, the test piece including the notch portion,
wherein the load applying device is configured to apply the load to the test piece held by the pair of holding jigs.

23. The apparatus for evaluating a semiconductor wafer according to claim 22, wherein each of the pair of holding jigs is provided with a cut through which a vicinity of the notch portion is exposed.

24. The apparatus for evaluating a semiconductor wafer according to claim 22, wherein the load applying device is further capable of applying a load to an edge of a test piece and breaking the edge by the load, the test piece including no notch portion and being cut from the semiconductor wafer to be evaluated.

* * * * *